United States Patent
Baigent et al.

(10) Patent No.: US 9,416,427 B2
(45) Date of Patent: *Aug. 16, 2016

(54) ASSAY METHODS FOR MDV-1

(71) Applicant: Zoetis Services LLC, Florham Park, NJ (US)

(72) Inventors: Susan Baigent, Reading (GB); Venugopal Nair, Oxford (GB); Herve Le Galludec, Ploemeur (FR)

(73) Assignee: Zoetis Services LLC, Florham Park, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/467,856

(22) Filed: Aug. 25, 2014

(65) Prior Publication Data

US 2015/0024382 A1 Jan. 22, 2015

Related U.S. Application Data

(62) Division of application No. 13/391,563, filed as application No. PCT/GB2010/001602 on Aug. 25, 2010, now Pat. No. 8,865,409.

(30) Foreign Application Priority Data

Aug. 25, 2009 (GB) .................................. 0914826.3

(51) Int. Cl.
C12Q 1/68 (2006.01)
C12Q 1/70 (2006.01)

(52) U.S. Cl.
CPC .......... C12Q 1/705 (2013.01); C12Q 2600/156 (2013.01)

(58) Field of Classification Search
None
See application file for complete search history.

(56) References Cited

U.S. PATENT DOCUMENTS

2012/0208177 A1   8/2012   Baigent et al.

FOREIGN PATENT DOCUMENTS

CN   101824488 A   9/2010
EP   0775743 A2   5/1997

OTHER PUBLICATIONS

Baigent et al. (Replication kinetics of Marek's disease vaccine virus in feathers and lymphoid tissues using PCR and virus isolation, J Gen Virol. Nov. 2005;86(Pt 11):2989-9).*
Spatz et al. (Comparative full-length sequence analysis of oncogenic and vaccine (Rispens) strains of Marek's disease virus, J Gen Virol. Apr. 2007;88(Pt 4):1080-96).*
Lee et al. (Characterization of a very Virulent Mareks Disease Virus Mutant Expressing the pp38 Protein from the Serotype 1 Vaccine Strain CVI988/Rispens, Virus Genes. Aug. 2005;31(1):73-80).*
NCBI Accession No. DQ530348 (Mar. 22, 2007).*
NCBI Accession No. EF523390 (Oct. 29, 2007).*
Nolan et al. (Quantification of mRNA using real-time RT-PCR, Nature Protocols, vol. 1, No. 3, Nov. 9, 2006).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Stratagene (Gene Characterization Kits; 1988).*
Weiner et al. (Kits and their unique role in molecular biology: a brief retrospective, BioTechniques 44:701-704 (25th Anniversary Issue, Apr. 2008)).*
Kozdrún (Development of Multi PCR for Detection of Marek's Disease Virus Strains, Medycyna Wet. Dec. 2005, 61 (6), p. 711-714).*
Baigent, S. J., et al., "Absolute quantitation of Marek's disease virus genome copy number in chicken feather and lymphocyte samples using real-time PCR," J. Virol. Methods., vol. 123, No. 1, pp. 53-64, 2005 [available online Oct. 22, 2004].
Baigent, S. J., et al., "Replication kinetics of Marek's disease vaccine virus in feathers and lymphoid tissues using PCR and virus isolation," J. Gen. Virol., vol. 86, pp. 2989-2998, 2005.
Baigent, S. J., et al., "Vaccinal control of Marek's disease: Current challenges, and future strategies to maximize protection," Vet. Immunol. Immunopathol., vol. 112, pp. 78-86, 2006.
Becker, Y., et al., "Polymerase chain reaction for differentiation between pathogenic and non-pathogenic scrotype 1 Marek's disease viruses (MDV) and vaccine viruses of MDC-serotypes 2 and 3," J. Virol. Methods, vol. 40, pp. 307-322. 1992.
Bülow, V.V., et al., German article from *Zentralblatt für Veterinarmedizin*, B, vol. 23, pp. 391-402, 1976 [***English summary is found on p. 400].
Fakhrul Islam, A. F. M., et al., "Relationship between Marek's disease virus load in peripheral blood lymphocytes at various stages of infection and clinical Marek's disease in broiler chickens," Avian Pathology, vol. 35, No. 1, pp. 42-48, 2006.

(Continued)

*Primary Examiner* — Aaron Priest
(74) *Attorney, Agent, or Firm* — Gloria K. Szakiel

(57) ABSTRACT

A method for the quantification of a vaccine strain and/or a virulent strain of Marek's Disease Virus Serotype-1 (MDV-1) in a sample from a bird, comprising the steps of: (i) providing a biological sample from the bird and optionally isolating nucleic acid from the biological sample; (ii) subjecting the biological sample of (i) to real-time quantitative PCR (qPCR) comprising: (a) amplification of a region of the pp38 gene within the nucleic acid sample of (i), said region containing a consistent single nucleotide polymorphism (SNP) difference between vaccine and virulent strains of MDV-1; and (b) contacting the amplified nucleic acid of (a) with a detectable nucleic acid probe specific for the SNP of the vaccine strain of MDV-1 and/or a detectable nucleic acid probe specific for the SNP of the virulent strain of MDV-1; and (iii) Measuring changes in the detectable signal produced by the probe of (ii). Methods are also provided for the absolute quantification of vaccine and virulent viruses.

8 Claims, 15 Drawing Sheets

(56) References Cited

OTHER PUBLICATIONS

Islam, A., et al., "Absolute quantitation of Marek's disease virus and Herpesvirus of turkeys in chicken lymphocyte, feather tip and dust samples using real-time PCR," J. Virol. Methods, vol. 132, pp. 127-134, 2006 [available online Nov. 14, 2005].

Islam, A., et al., "Addendum to 'Absolute quantitation of Marek's disease virus and Herpesvirus of turkeys in chicken lymphocyte, feather tip and dust samples using real-time PCR,'" J. Virol. Methods, vol. 141, p. 230, 2007.

De Boer, G. F., et al., "Protective Efficacy of Marek's Disease Virus (MDV) CVI-988 CEF65 Clone C against Challenge Infection with Three Very Virulent MDV Strains," Avian Diseases, vol. 30, No. 2, pp. 276-283, Apr.-Jun. 1986.

Gimeno, I. M., et al., "The pp38 Gene of Marek's Disease Virus (MDV) Is Necessary for Cytolytic Infection of B Cells and Maintenance of the Transformed State but Not for Cytolytic Infection of the Feather Follicle Epithelium and Horizontal Spread of MDV," J. Virol., vol. 79, No. 7, pp. 4545-4549, 2005.

Handberg, K. J., et al., "The use of serotype 1- and serotype 3-specific polymerase chain reaction for the detection of Marek's disease virus in chickens," Avian Pathology, vol. 30, No. 3, pp. 243-249, 2001.

King, D., et al., "Difference between Influences of Homologous and Heterologous Maternal Antibodies on Response to Serotype-2 and Serotype-3 Marek's Disease Vaccines," Avian Diseases, vol. 25, No. 1, pp. 74-81, Jan.-Mar. 1981.

Landman, W. J. M. & S. B. E. Verschuren, "Titration and Marek's Disease Cell-Associated Vaccine Virus (CVI 998) of Reconstituted Vaccine and Vaccine Ampoules from Dutch Hatcheries," Avian Diseases, vol. 47, No. 4, pp. 1458-1465, Oct.-Dec. 2003.

Renz, K. G., et al., "Absolute quantification using real-time polymerase chain reaction of Marek's disease virus serotype 2 in field dust samples, feather tips and spleens," J. Virol. Methods, vol. 135, pp. 186-191, 2006 [available online May 6, 2006].

Rispens, B. H., et al., "Control of Marek's Disease in the Netherlands. I. Isolation of an Avirulent Marek's Disease Virus (Strain CVI 998) and Its Use in Laboratory Vaccination Trials," Avian Diseases, vol. 16, No. 1, pp. 108-125, Apr. 1972.

Silva, R. F., "Differentiation of Pathogenic and Non-Pathogenic Serotype 1 Marek's Disease Viruses (MDVs) by the Polymerase Chain Reaction Amplification of the Tandem Direct Repeats within the MDV Genome," Avian Diseases, vol. 36, No. 3, pp. 521-528, Jul.-Sep. 1992.

Witter, R. L., et al., "Classification of Marek's disease viruses according to pathotype: philosophy and methodology," Avian Pathology, vol. 34, No. 2, pp. 75-90, 2005.

Shamblin, C.E., et al., "Comparative analysis of Marek's disease virus (MDV) glycoprotein-, lytic antigen pp38- and transformation antigen Meq-encoding genes: association of *meq* mutations with MDVs of high virulence," Veterinary Microbiology, vol. 102, No. 3-4, pp. 147-167, Sep. 8, 2004.

Spatz, S.J., et al., "Sequence determination of variable regions within the genomes of gallid herpesvirus-2 pathotypes," Archives of Virology, vol. 152, No. 9, pp. 1665-1678, Jun. 8, 2007.

Spatz, S.J., et al., "Comparative full-length sequence analysis of oncogenic and vaccine (Rispens) strains of Marek's disease virus," Journal of General Virology, vol. 88, No. Part 4, pp. 1080-1096, Apr. 2007.

Endoh, D., et al., Database EMBL [Online], "Marek disease virus type 1 pp38 mRNA, complete eds.," XP002609232, retrieved from EBI Database accession No. S76060, Aug. 4, 1995.

Zhizhong et al. (Analyzing the H19- and T65-epitopes in 38 kd phosphorylated protein of Marek's disease viruses and comparing chicken immunological reactions to viruses point-mutated in the epitopes, Science in China Ser. C Life Sciences 2004 vol. 47 No. 1 82-91).

Edwards et al. (Mutation Detection by Real-Time PCR, available at http://www.horizonpress.com/pcr/pdf/rtpcr/rtpcr08.pdf, Jul. 26, 2008).

Baigent et al. (Absolute quantitation of Marek's disease virus genome copy number in chicken feather and lymphocyte samples using real-time PCR, Journal of Virological Methods 123 (2005) 53-64).

Baigent et al. (hereinafter "Baigent 2"; Correlation of Marek's disease herpesvirus vaccine virus genome load in feather tips with protection, using an experimental challenge model, Avian Pathology, 36:6, 467-474, 2007).

AllGlo Technology for Real Time PCR (hereinafter "AllGlo"; available at http://www.allelogic.com/product.htm, May 30, 2008).

Renz et al. (Differentiation between pathogenic serotype 1 isolates of Marek's disease virus and the Rispens CVI998 vaccine in Australia using real-time PCR and high resolution melt curve analysis, Journal of Virological Methods 187 (2013) 144-152.

Sigma-Aldrich Life Science, qPCR Technical Guide, Detection Methods Primer and Probe Design Instrumentation Applications Guide, pp. 2-43, 2008.

\* cited by examiner

FIG. 1A

CVI988 (vaccine strain)

ATGGAATTCGAAGCAGAACACGAAGGGCTGACGGCGTCTTGGGTCGCCCCCGCTCCC
CAGGGTGGAAAAGGGCCGGAGGGCGGCGCAGGGGTCGCCGACGAGGCAGGGCATGGG
AAAACAGAAGCGGAATGCCGAGGGCCCGAGGGCCGAGAAATGCGGGGACGCCGAGATGAGC
GCTTTGGATCGGGTCCAGAGGGACCGGTGGAGATTCAGTTCTCCGCCCCTCACTCT
GGAGTCACGGGAAGGGGGCTATTCCAATAAAGGGTGATGGGAAGGCGATAGAATGC
CAGGAGCTAACCGGAGAGGGAGAGTGGCTGTCACGGTGGGGGGAGCTACCGCCTGA
GCCCCGGAGGTCAGGGAATGAACATCTTGACGAAAGTCGGTATGCGAAACAAACCGA
AAGGGGTAGCTCTACCGGGAAAGAGGAACATATGCCGACTTGCTTGTCGAAGCAGAGCAAGC
TGCCCAGCAGTGCCAAGGAGGAACATATGCCGACTTGCTTGTCGAAGCAGAGCAAGC
TGTTGTACATTCCGTTCGCGCATTAATGCTGGCCGAAAGACAAAACCCAAATATATT
GGGGGAGCATTTGAATAAAAAACGGGTTCTTGTACAACGACCCCGTACTATTCTATC
CGTGGAGTCAGAGAATGCAACAATGCGTTCTGTTCGGCATGTCATTTTTCGCTGGTATGTTAGTCGG
TGCAAAATCATTATTACTAGGATCGTGCATGTCATTTTTCGCTGGTATGTTAGTCGG
TAGAACGGCAGACGTAAAAACACCATTATGGGATACTGTATGTTTGTTAATGGCTTT
CTGTGCAGGCATTGTCGTTGGGGAGTGGATTCTCGGGGAGGTGAATTCTGGAGAAAC
AAAATCTGAATCAAATTAA SEQ ID NO. 10

FIG. 1B

Md5 (representative virulent strain)

ATGGAATTCGAAGCAGAACACGAAGGGCTGACGGCGTCTTGGGTCGCCCCCGCTCCC
CAGGGTGGAAAAGGGGCGGAGGGCCGCGCAGGGGTCGCCGACGAGGCAGGGCATGGG
AAAACAGAAGCGGAATGCGCCGAGGACGGCGAGAAATGCGGGGACGCCGAGATGAGC
GCTTTGGATCGGGTCCAGAGGGACCGGTGGAGATTCAGTTCTCCGCCCCCTCACTCT
GGAGTCACGGGGAAGGGGGCTATTCCAATAAAGGGTGATGGGAAGGCGATAGAATGC
CAGGAGCTAACCGGAGAGGGAGAGTGGCTGTCACAGTGGGAGGAGCTACCGCCTGA
GCCCCGGAGGTCAGGGAATGAACATCTTGACGAAAGTCGGTATGCGAAACAAACCGA
AAGGGGTAGCTCTACGGGGAAAGAAGAGGGAGATGGTATGAAGCAGATGGGGGAGCT
TGCCCAGCAGTGCGAAGGAGGAACATATGCGGACTTGCTTGTCGAAGCAGAGCAAGC
TGTTGTACATTCCGTTCGCGCATTAATGCTGGCCGAAAGACAAAACCCAAATATATT
GGGGGAGCATTTGAATAAAAAACGGGTTCTTGTACAACGACCCCGTACTATTCTATC
CGTGGAGTCAGAGAATGCAACAATGCGTTCTTATATGCTGGTTACATTGATCTGTTC
TGCAAAATCATTATTACTAGGATCGTGCATGTCATTTTTCGCTGGTATGTTAGTCGG
TAGAACGGCAGACGTAAAAACACCATTATGGGATACTGTATGTTTGTTAATGGCTTT
CTGTGCAGGCATTGTCGTTGGGGGAGTGGATTCTGGGGAGGTGGAATCTGGAGAAAC
AAAATCTGAATCAAATTAA SEQ ID NO. 11

FIG. 4

Specificity of CVI MDV1-specific and virulent MDV1-specific q-PCRs pCVI988 vaccine

FIG. 8A

| Bird # | Vaccine virus | | Challenge virus | | | Total virus | | Group |
|---|---|---|---|---|---|---|---|---|
| | CVI pp38 | BAC | Vir pp38 | US2 | Pp38 total | Total virus CVI pp38 + Vir pp38 | BAC + US2 | |
| 7 | 0.6 | 0.6 | 0.6 | 0.6 | 0.6 | 0.6 | 0.6 | 1 |
| 8 | 0.6 | 0.6 | 0.6 | 0.6 | 0.6 | 0.6 | 0.6 | 1 |
| 9 | 0.6 | 0.6 | 0.6 | 0.6 | 0.6 | 0.6 | 0.6 | 1 |
| 10 | 0.6 | 0.6 | 0.6 | 0.6 | 0.6 | 0.6 | 0.6 | 1 |
| 20 | 0.6 | 0.6 | 10.4133 | 0.610321 | 6.3400262 | 11.013267 | 1.210321 | 1 |
| 33 | 12.08422 | 6.86523 | 0.6 | 0.6 | 6.217141 | 12.684216 | 7.465229 | 2 |
| 34 | 73.89111 | 41.9362 | 0.6 | 0.6 | 69.505476 | 74.491108 | 42.53621 | 2 |
| 35 | 108.9216 | 62.8334 | 0.6 | 0.6 | 135.02325 | 109.52162 | 63.43342 | 2 |
| 36 | 38.44967 | 20.1465 | 0.6 | 0.6 | 46.563351 | 39.049666 | 20.74648 | 2 |
| 37 | 27.04878 | 14.1326 | 0.6 | 0.6 | 15.608305 | 27.648783 | 14.73263 | 2 |
| 38 | 22.07838 | 10.8055 | 0.6 | 0.6 | 11.909725 | 22.678378 | 11.40551 | 2 |
| 39 | 66.8376 | 30.4068 | 0.6 | 0.6 | 40.047342 | 67.437598 | 31.00682 | 2 |
| 40 | 91.48551 | 42.5222 | 0.6 | 0.6 | 66.834552 | 92.085513 | 43.1222 | 2 |
| 57 | 46.02852 | 37.5797 | 0.6 | 0.6 | 25.292471 | 46.62852 | 38.17967 | 2 |
| 58 | 40.31057 | 19.7312 | 0.6 | 0.6 | 22.422805 | 40.910566 | 20.33119 | 2 |
| 59 | 22.5008 | 17.3914 | 0.6 | 0.6 | 23.53557 | 23.100805 | 17.99143 | 2 |
| 60 | 26.0569 | 15.2566 | 0.6 | 0.6 | 32.832402 | 26.656902 | 15.85664 | 2 |
| 73 | 53.56301 | 29.4951 | 0.6 | 0.6 | 29.989807 | 54.163009 | 30.09514 | 3 |
| 74 | 2.756061 | 2.31151 | 0.6 | 0.6 | 0.7493988 | 3.3560606 | 2.911508 | 3 |
| 75 | 111.9461 | 60.3714 | 0.6 | 0.6 | 69.592823 | 112.54611 | 60.97139 | 3 |
| 76 | 25.80373 | 13.5721 | 0.6 | 0.6 | 9.7218418 | 26.403734 | 14.17206 | 3 |

See continuation on Fig 8B

FIG. 8B Continuation from Fig 8A

| Bird # | Vaccine virus | | Challenge virus | | Pp38 total | Total virus CVI pp38 + Vir pp38 | Total virus BAC + US2 | Group |
|---|---|---|---|---|---|---|---|---|
| | CVI pp38 | BAC | Vir pp38 | US2 | | | | |
| 77 | 95.00511 | 43.0761 | 0.6 | 0.6 | 89.788494 | 95.605107 | 43.67613 | 3 |
| 78 | 34.57861 | 14.7835 | 0.6 | 0.6 | 29.559124 | 35.178607 | 15.38354 | 3 |
| 79 | 209.1736 | 79.0153 | 0.6 | 0.6 | 91.518889 | 209.77359 | 79.61528 | 3 |
| 80 | 74.00517 | 31.7329 | 0.6 | 0.6 | 30.167914 | 74.60517 | 32.33293 | 3 |
| 53 | 0.6 | 6.53149 | 186.441 | 105.8535 | 157.3787 | 187.04092 | 112.385 | 3 |
| 54 | 23.60337 | 13.3084 | 0.6 | 0.6 | 19.567058 | 24.203367 | 13.90842 | 3 |
| 55 | 0.6 | 0.6 | 520.435 | 292.1547 | 180.2854 | 521.03523 | 292.7547 | 3 |
| 56 | 0.6 | 8.65401 | 135.14 | 70.7959 | 61.833435 | 135.73995 | 79.4499 | 3 |
| 97 | 27.61513 | 36.576 | 257.743 | 181.7754 | 139.91434 | 285.35809 | 218.3515 | 3 |
| 98 | 93.3635 | 77.5982 | 17.4293 | 24.81795 | 72.023249 | 110.79276 | 102.4162 | 3 |
| 113 | 0.6 | 0.6 | 153.463 | 114.0614 | 56.894591 | 154.06313 | 114.6614 | 4 |
| 114 | 0.6 | 0.6 | 657.876 | 492.0194 | 491.5686 | 658.47595 | 492.6194 | 4 |
| 115 | 0.6 | 0.6 | 658.286 | 556.68 | 469.6545 | 658.88565 | 557.28 | 4 |
| 116 | 0.6 | 0.6 | 1695.07 | 1862.283 | 801.4807 | 1695.6744 | 1862.883 | 4 |
| 117 | 0.6 | 0.6 | 508.742 | 430.4008 | 193.58847 | 509.34249 | 431.0008 | 4 |
| 118 | 0.6 | 0.6 | 3138.3 | 4560.695 | 1440.8261 | 3138.9007 | 4561.295 | 4 |
| 119 | 0.6 | 0.6 | 970.272 | 784.7185 | 307.26794 | 970.87209 | 785.3185 | 4 |
| 120 | 0.6 | 0.6 | 2759.31 | 3795.307 | 1115.4084 | 2759.9081 | 3795.907 | 4 |
| 127 | 0.6 | 0.6 | 22066.3 | 64459.18 | 24699.696 | 22066.918 | 64459.78 | 4 |

Comparison of two qPCRs to measure pCVI988 vaccine virus: All vaccinated birds

Comparison of two qPCRs to measure RB-1B challenge virus: All vaccinated birds

ASSAY METHODS FOR MDV-1

CROSS-REFERENCE TO RELATED APPLICATIONS

This application is a divisional of U.S. application Ser. No. 13/391,563, filed Apr. 29, 2012, which is a US National Stage Entry of International Application No. PCT/GB2010/001602, filed Aug. 25, 2010, which claims the benefit of GB provisional Application No. 0914826.3, filed Aug. 25, 2009, the entire contents each of which are incorporated herein by reference in their entirety.

FIELD OF THE INVENTION

The present invention relates to assay methods and, in particular, to methods for analysing levels of vaccine strains and levels of virulent strains of virus, particularly Marek's Disease Virus serotype-1 (MDV-1), in samples from birds.

BACKGROUND

Marek's Disease Virus (MDV) is a herpesvirus, which causes lymphoproliferative disease in chickens. Even after the introduction of vaccines against MDV, the infection still causes considerable losses in the poultry industry. MDV is divided into three serotypes, all of which establish latent infections. Serotype 1 includes oncogenic viruses, serotype 2 non-oncogenic viruses and serotype 3 includes the turkey herpesviruses (HVT) (Bülow et al (1976) Zentralblatt für Veterinarmedizin, 23B, 391-402).

Handberg et al (2001) Avian Pathology 30: 243-249 describe the use of serotype 1- and serotype 3-specific PCR for the detection of MDV in chickens. Tissue samples were taken from blood (buffy-coat cells), spleen, liver, skin, feather tips and ovaries.

CVI988 (Rispens) strain, a naturally-attenuated MDV serotype-1 (MDV-1), was introduced in the mid-1990s (Rispens et al., (1972) Avian Diseases, 16, 108-125; de Boer et al., (1986) Avian Diseases, 30, 276-283) and is to-date the most effective vaccine against MDV. However, even in light of vaccination programmes, MDV outbreaks continue to cause significant losses. These outbreaks can have several causes including: inhibition by maternal antibodies of vaccine virus replication (King et al., (1981) Avian Diseases, 25, 74-81; de Boer et al., (1986) supra); suppression of the immune response to vaccine by environmental stresses or co-infections with immunosuppressive pathogens; infection with a virulent MDV strain prior to establishment of full vaccinal immunity; infection of vaccinated and fully immunocompetent birds with a hypervirulent MDV strain (Witter et al., (2005) Avian Pathology, 34, 75-90); and, finally, administration of insufficient vaccine dose which fails to induce protective immunity.

As such it is important to be able to accurately measure MDV vaccine and challenge (virulent) virus individually, including measuring one or both, in the same individual chicken for both experimental and commercial reasons. Experimentally, it is very useful to be able to examine the interactions between vaccine and challenge virus, with a view to better understanding the mechanism of vaccinal protection and differences in efficiency between vaccines. Commercially, it is important to assist in identifying the causes of vaccine failures, such as administration of a sub-optimal vaccine dose (Landman & Verschuren, 2003), interference with vaccine virus replication by maternal antibodies (King et al., 1981; de Boer et al., 1986), and infection with hypervirulent MDV field strains (Witter et al., 2005).

A highly sensitive real-time quantitative PCR (q-PCR) assay for absolute quantitation of MDV-1 in chicken tissues has been developed (Baigent et al., 2005a) and used very successfully to investigate the kinetics of CVI988 vaccine virus replication in tissues of experimental and commercial chicks in the absence of challenge virus infection (Baigent et al., 2005b, 2006). However this method cannot distinguish between CVI988 and challenge virus. Other groups have developed real-time PCR assays to quantify MDV-2 (Renz et al., 2006) and MDV-3 (herpesvirus of turkeys) (Islam et al., 2006a). These serotype-specific assays can be used to quantify both vaccine and virulent challenge virus in individual chickens, where challenge virus (always MDV-1) is of a different serotype to vaccine virus (MDV-2 or -3) (Islam et al., 2006b).

However, the most widely used and effective MDV vaccine is a naturally-attenuated serotype-1 strain (CVI988, Rispens) (Rispens et al., 1972; de Boer et al., 1986) and, to date, real-time PCR to distinguish challenge virus from serotype-1 vaccine virus has not been possible, because sequence differences between them are very limited. A difference in the number of repeats in the 132-bp repeat region can be used to distinguish CVI988 from virulent strains using conventional PCR (Becker et al., 1992; Silva, 1992). However, the repetitive nature of this region precludes its use in quantitative PCR. Differences in the meq gene and the ICP4 gene are not consistent between CVI988 and virulent strains. A qPCR system has also been developed (Baigent, unpublished) to distinguish between BAC (Bacterial Artificial Chromosome) cloned MDV-1 and wild-type MDV-1 by targeting the BAC-specific sequence of the BAC cloned MDV-1 and US2 gene of the wild-type MDV-1, this can be used to distinguish between BAC cloned vaccine strains and wild-type virulent strains but only when such vaccine stains are BAC cloned. Importantly, such a method could not be used commercially, since no commercial MDV-1 vaccines are BAC cloned.

The pp38 gene shows a consistent single nucleotide difference between the CVI988 vaccine strain and virulent strains of MDV-1, however q-PCR primers are difficult to design which would be able to distinguish such a small difference.

DESCRIPTION OF THE INVENTION

The present invention provides methods for quantifying vaccine and/or virulent MDV-1 strains of Marek's Disease Virus Serotype-1 in birds based on a single nucleotide polymorphism (SNP) in the pp38 gene. These methods also include methods for the quantification of the relative and/or absolute amounts of vaccine and virulent strains and determination of copy number of each strain.

In a first aspect the invention provides a method for the quantification of a vaccine strain of Marek's Disease Virus Serotype-1 (MDV-1) in a sample from a bird, comprising the steps of:
  (i) providing a biological sample from the bird;
  (ii) subjecting the biological sample of (i) to real-time quantitative PCR (qPCR) comprising:
    (a) amplification of a region of the pp38 gene within the nucleic acid sample of (i), said region containing a consistent single nucleotide polymorphism (SNP) difference between vaccine and virulent strains of MDV-1; and
    (b) contacting the amplified nucleic acid of (a) with a detectable nucleic acid probe specific for the SNP of the virulent strain of MDV-1;

(iii) Measuring changes in the detectable signal produced by the probe of (ii)

In a second aspect the invention provides a method for the quantification of a virulent strain of Marek's Disease Virus Serotype-1 (MDV-1) in a sample from a bird, comprising the steps of:
(i) providing a biological sample from the bird;
(ii) subjecting the biological sample of (i) to real-time quantitative PCR (qPCR) comprising:
  (a) amplification of a region of the pp38 gene within the nucleic acid sample of (i), said region containing a consistent single nucleotide polymorphism (SNP) difference between vaccine and virulent strains of MDV-1; and
  (b) contacting the amplified nucleic acid of (a) with a detectable nucleic acid probe specific for the SNP of the virulent strain of MDV-1;
(iii) Measuring changes in the detectable signal produced by the probe of (ii)

In a third aspect the invention provides a method for the quantification of a vaccine strain and a virulent strain of Marek's Disease Virus Serotype-1 (MDV-1) in a sample from a bird, comprising the steps of:
(i) providing biological samples from the bird;
(ii) subjecting the biological samples of (i) to real-time quantitative PCR (qPCR) comprising:
  (a) amplification of a region of the pp38 gene within the nucleic acid samples of (i), said region containing a consistent single nucleotide polymorphism (SNP) difference between vaccine and virulent strains of MDV-1; and
  (b) contacting the amplified nucleic acid of (a) with a detectable nucleic acid probe specific for the SNP of the vaccine strain and a second nucleic acid probe specific for the SNP of the virulent strain of MDV-1;
(iii) Measuring changes in the detectable signal produced by each probe of (ii); and optionally
(iv) comparing the changes in the detectable signal measured in (iii) for each specific probe.

In one embodiment of the invention the quantification of the virulent and vaccine strains may be a relative quantification.

The methods of the invention optionally may include the step of isolating nucleic acid from the biological sample of step (i) and subjecting the isolated nucleic acid to the qPCR of step (ii).

The biological sample provided from the bird may comprise bird nucleic acid or nucleic acid as isolated from the bird (i.e. may include both bird nucleic acids and nucleic acid from other sources within the bird—e.g. a virus). In one embodiment of the invention the biological sample provided is derived from the following tissues: blood, spleen, liver, skin, ovaries, bursa, thymus, kidney or feather tips of individual birds (Baigent et al., (2005a) Journal of Virological Methods, 23, 53-64; Baigent et al., (2005b) *Journal of General Virology*, 86, 2989-2998). Use of feather tips provides a means of sampling birds in the field and is the simplest and least invasive procedure.

The pp38 gene encodes a phosphoprotein that plays an important role in the pathogenesis of MDV. The pp38 gene has been shown to be necessary to establish cytolytic infection in B-cells, to produce an adequate level of latently infected T-cells and to maintain the transformed state in vivo. (Gimeno et al. 2005)

A single-nucleotide polymorphism (SNP) is a DNA sequence variation occurring when a single nucleotide (A, T, C, or G) in the genome (or other shared sequence) differs between members of a species, or between paired chromosomes in an individual, or in this case between vaccine and virulent strains of MDV-1. For example, two sequenced DNA fragments from different individuals, AAGCCTA to AAGCTTA, contain a difference in a single nucleotide. In this case we say that there are two alleles, the C polymorphism and the T polymorphism. Almost all common SNPs have only two alleles.

Real-time polymerase chain reaction, also called quantitative real time polymerase chain reaction (Q-PCR/qPCR) or kinetic polymerase chain reaction is a technique based on the polymerase chain reaction (PCR) and is used to both amplify and quantify target genetic material. qPCR enables both detection and quantification (as relative amount or absolute number of copies when normalized to DNA input or additional normalizing genes) of a specific sequence in a DNA sample. qPCR follows the general procedure of PCR with the extra feature that the accumulating amplified DNA is quantified in real time after every cycle of the qPCR. Such quantification can be achieved by the common methods of fluorescing agents that intercalate with the accumulating DNA or modified nucleic acid probes complimentary to the amplified DNA sequence that produce a detectable signal on binding with the accumulating DNA. Therefore qPCR is a widely used and very useful method of detecting and quantifying a particular nucleic acid sequence in a sample. Methods of qPCR are well known to those skilled in the art and are described in textbooks such as Sambrook and Russell, Molecular Cloning: a Laboratory Manual. Volumes 1, 2 and 3 (2001, $3^{rd}$ Edition).

Here a method is provided for detecting vaccine and/or virulent strains of MDV-1 in a nucleic acid sample through the means of Real-Time PCR (qPCR) and using an agent such as a nucleic acid probe capable of producing a detectable signal upon binding with the nucleic acid produced during the qPCR. Such a detectable signal may conveniently be provided by labelling the probe with a fluorescing dye such as JUP which has a wavelength detectable in the VIC detection channel of the qPCR instrument.

To achieve specificity in a duplex assay (i.e. an assay with two forms of nucleic acid to be detected) specificity is usually required at three levels:
(1) PCR product specificity: In the present invention a universal primer pair is used, complimentary to a conserved region of the pp38 gene, and as a result both CVI988 and virulent strains of MDV-1 will be amplified equally and as such there is no specificity at this level.
(2) Probe specificity: In the present invention there is good probe specificity, since both probes bind minimally to the mis-matched PCR product, instead binding specifically to either the vaccine or virulent strains of MDV-1.
(3) Detector specificity: In the present invention there is no cross talking between the detection channels of the known standard reaction and the pp38 reaction and as such detector specificity is achieved.

The detectable signal produced during the qPCR may be provided by labelling the probe with any agent capable of producing a detectable signal such as a fluorescing agent such as a fluorescent dye, for example MAR, JUP, NEP, SAT, URA, FAM, HEX, TET, VIC, JOE, TAMRA, ethidium bromide, LC Green, SYBR Green I, YO-PRO-1, BEBO and SYTO9; a chromophore, such as a chromophore dye, for example Cy3, Cy5, Pyr(10)PC; or a chromophore dye pair suitable for use in FRET analysis for example the dye pair TOTO 1 and TOTO 3.

In a further embodiment of the invention the quantification of the strain(s) is absolute quantification. In one embodiment of the invention, the qPCRs of step (ii) further comprise a concomitant known standard qPCR (normalisation reaction) utilising a probe labelled with a different detectable signal to allow absolute quantification of the attenuated and/or virulent strains. The different detectable signal allows the signal produced to be detected in a separate detection channel of the qPCR instrument. In one embodiment this standard qPCR system is the Ovo reaction, which uses the Ovo host gene present in chicken DNA and conveniently may use the detectable signal FAM-BHQ1 (available from suppliers such as Eurogentec). Such a normalisation reaction allows accurate comparison of samples by taking account of the amount of DNA used in the reaction. Ovo is a gene present in chicken DNA and two copies of Ovo gene is equivalent to one cell, so the Ovo standard curve can be used to calculate the Ovo Ct value which is equivalent to 10000 cells. For the test samples, a standard curve produced using CVI988 DNA and the CVI988-specific reaction is used to calculate the copy no. (from CVI988-specific Ct value) of CVI988 in the sample, while a standard curve produced using RB-1B DNA and the virulent-specific reaction is used to calculate the copy no. (from virulent-specific Ct value) of virulent MDV in the sample. The Ovo standard curve is used to work out Ovo copy no. (from Ovo Ct value) in the sample. Ovo copy number (i.e. cell number) will be different in different samples so, in order to be able to accurately compare sample A with sample B it is calculated how many MDV copies would be in each sample if those samples had 10000 cells.

Using the signal provided by the aforementioned nucleic acid probe, the amount of DNA amplified by each cycle is quantifiable by comparison with the known standard. A cycle-threshold (Ct) value is produced as to allow the comparison of relative amounts of DNA produced for different samples. This Ct value is effectively a measure of the cycle of the qRT-PCR where the signal produced passes beyond a background threshold value.

This measurement is determined by plotting relative concentrations of DNA present during the exponential phase of the PCR reaction (measured as fluorescence) against cycle number on a logarithmic scale (so an exponentially increasing quantity will give a straight line). A threshold for detection of fluorescence above background is determined and the cycle at which the fluorescence from a sample crosses the threshold is the cycle threshold, Ct.

In other words, the Ct value is defined as the cycle number at the threshold level of log based fluorescence (i.e. the lowest fluorescence observed above background levels). This is the observed and measured value in real-time PCR experiments (qPCR).

The production of a detectable signal in a qPCR with each of the specific probes (one specific for the attenuated vaccine strain and one specific for a virulent strain of MDV-1) allows relative determination of the amount of each of the vaccine strain and the MDV-1 virulent strain in the nucleic sample provided from a specific bird. This is possible as the nucleic acid probes have a sequence complimentary to the sequence specific for either the vaccine or virulent strains of MDV-1 and accordingly will only bind to one of the specific strains. In the embodiment of the invention which includes a known standard, Ct values can be calculated as described and used in absolute quantification of the specific strain of virus produced in the qPCR reaction and as such a comparison of the amount of each strain is possible.

In one embodiment of the invention the vaccine strain of MDV-1 is an attenuated vaccine and in a further embodiment the vaccine strain is the attenuated vaccine CVI988.

Virus vaccines are dead, inactivated or attenuated forms of viruses or purified products derived from them and are given to a subject in order to induce an immune response to such a virus without the subject experiencing the usual negative effects or illness caused by the virus in its virulent form. Following such an immune response, immunity is created in the subject against exposure to the pathogen in its virulent form.

Several types of vaccine may be used and they represent different strategies used to try to reduce risk of illness, while retaining the ability to induce a beneficial immune response. Commonly used virus vaccines fall into the categories of killed vaccines, attenuated vaccines, toxoid vaccines, subunit vaccines and conjugate vaccines.

Attenuated vaccines contain live attenuated viruses—these are live viruses that can replicate. They are naturally occurring in a non-virulent form or have been cultivated under conditions that disable their virulent properties, or which use closely-related but less dangerous organisms to produce a broad immune response. They typically provoke more durable immunological responses than other forms of vaccine.

In one embodiment of the invention, the probes are complimentary to a sequence of pp38 incorporating the region of up to 30 base pairs around the SNP.

In a particular embodiment of the invention the probes may contain within a longer sequence or comprise solely of the following sequences or a fragment thereof:

```
Vaccine strain-specific probe:
                                        (SEQ ID NO: 1)
5' CCCACCGTGACAGCC 3'

Virulent strain-specific probe:
                                        (SEQ ID NO: 2)
5' CCCACTGTGACAGCC 3';
or a second virulent strain-specific probe:
                                        (SEQ ID NO: 3)
5' CTCCCACTGTGACAGCC 3'
```

In a further aspect of the invention, a method is provided wherein the qPCR of step (ii) further comprises the use of a 'total' nucleic acid probe in step (ii) capable of detecting both vaccine and virulent strains. Such a total probe is useful as a control as the amount of virus detected by the total probe should be equal to the sum of virus detected by both the vaccine-specific and virulent-specific probes in their specific qPCRs.

In a particular aspect of the invention the total probe specific for both strains may contain within a longer sequence or comprise solely of the following sequence or a fragment thereof:

```
                                        (SEQ ID NO: 4)
            5' GCTACCGCCTGAGCC 3'
```

The primers used within the qPCR will amplify a region incorporating the single nucleotide polymorphism and as such can be used in combination with any of the nucleic acid probes described above. In a preferred embodiment of the invention, the forward and reverse primers used in the amplification of the nucleic acid sample may contain within a longer sequence or comprise solely of the following sequences or a fragment thereof:

```
Forward primer:
                                             (SEQ ID NO: 5)
5' GAGCTAACCGGAGAGGGAGA 3'

Reverse primer:
                                             (SEQ ID NO: 6)
5' CGCATACCGACTTTCGTCAA 3'
```

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, 81%, 82%, 83%, 84%, more typically at least about 85%, 86%, 87%, 88%, 89%, more typically at least about 90%, 91%, 92%, 93%, 94%, and even more typically at least about 95%, 96%, 97%, 98%, 99% sequence identity to a polynucleotide recited above.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

Oligonucleotides as used in the present invention can be produced by methods routine to those skilled in the art and are discussed in text books such as Ch10 Molecular Cloning: A Laboratory Manual (Sambrook and Russell 2001).

As discussed, the specificity of the probes used is due to a consistent single nucleotide polymorphism (SNP) in the pp38 gene between attenuated and virulent strains of MDV-1. In an embodiment of the invention the probes used to detect this SNP are homolabelled fluorogenic probes comprising two identical reporter dyes that are capable of quenching each other and becoming dequenched once the probe is cleaved. Preferably such probes are AllGlo miniprobes (AlleLogic Biosciences Corp, Hayward, Calif.).

AllGlo miniprobes are novel homolabelled fluorogenic probes. Unlike conventional dual-labeled Taqman probes, AllGlo miniprobes are comprised of two identical reporter dyes that are capable of quenching each other and become dequenched once the probe is cleaved. Thus, probe cleavage results in the release of two signal-generating dyes per probe, increasing detection sensitivity compared with Taqman probes.

AllGlo miniprobes are significantly shorter than conventional dual-labeled probes (e.g. 15-16 nucleotides). The shortened length makes quenching more efficient and results in low fluorescent baselines. The specificity is greater than that of Taqman probes, such that an AllGlo miniprobe can detect a single point mutation. AllGlo miniprobes are preferably used with the fluorescing dyes MAR, JUP, NEP, SAT or URA available from Allelogic Biosciences.

In one embodiment of the invention, the virulent MDV-1 strain is selected from RB1B MDV, 584A MDV, 595 MDV, 684A MDV, Md5 MDV, HPRS-B14 MDV, JM102 MDV, 660A MDV, 675A MDV, 549 MDV, 571 MDV, or C12-130 MDV.

In one aspect the method of the invention may be used in the diagnosis of infection with virulent MDV-1 in birds whether or not they have been previously vaccinated with, for example, an attenuated vaccine strain. As the method has the ability to simultaneously monitor the behaviour of the vaccine and the virulent strains, it would be the diagnostic method of choice in situations such as identifying the cause of vaccine failures and in a further aspect the method may be used as a research tool in the development and/or testing of MDV-1 vaccines. The method may be particularly useful in common situations in which it is not known if a bird is infected with both vaccine and virulent strains prior to testing for either strain.

In one embodiment, the invention may be provided as a kit of parts comprising:

(i) primers that will amplify a region of the pp38 gene incorporating a consistent single nucleotide polymorphism (SNP) between vaccine and virulent strains of MDV-1; and (ii) a labelled nucleic acid probe for the pp38 polymorphism specific to the vaccine strain of MDV-1.

In a further embodiment, the invention may be provided as a kit of parts comprising:

(i) primers that will amplify a region of the pp38 gene incorporating a consistent single nucleotide polymorphism (SNP) between vaccine and virulent strains of MDV-1; and (ii) a labelled nucleic acid probe for the pp38 polymorphism specific to the virulent strains of MDV-1.

In a further embodiment, the invention may be provided as a kit of parts comprising:

(i) primers that will amplify a region of the pp38 gene incorporating a consistent single nucleotide polymorphism (SNP) between vaccine and virulent strains of MDV-1;

(ii) a labelled nucleic acid probe for the pp38 polymorphism specific to vaccine strain; and (iii) a labelled nucleic acid probe for the pp38 polymorphism specific to virulent strains of MDV-1.

In further embodiments the kit of parts may optionally include standard qPCR reagents and/or a known standard qPCR utilising a probe labelled with a different detectable signal. In one embodiment the vaccine strain quantified by the kit of parts is the CVI988 vaccine.

In a further embodiment the nucleic acid probe(s) of the kit of parts may contain within a longer sequence or comprise solely of the following sequences or a fragment thereof:

```
Vaccine strain-specific probe:
                                             (SEQ ID NO: 1)
5' CCCACCGTGACAGCC 3';
and/or Virulent strain-specific probe:
                                             (SEQ ID NO: 2)
5' CCCACTGTGACAGCC 3'
```

The kit of parts may further comprises a total probe that binds both vaccine strains and virulent strains which in one embodiment has the following sequence:

```
                                             (SEQ ID NO: 4)
        5' GCTACCGCCTGAGCC 3'
```

Preferred Embodiments

Examples embodying certain aspects of the invention will now be described with reference to the following figures in which:

FIGS. 1A and 1B show the binding location of primers bold underline and probes

[bold boxed]

in the ppm gene for (a) CVI988 (vaccine strain) of SEQ ID NO: 10 and (b) Md5 (representative virulent strain) of SEQ ID NO: 11, respectively. The probes binding the consistent polymorphism G/A are the specific probes, the other probe is the total probe. The G/A polymorphism is not consistent in all virulent strains FIGS. 2A and 2B show the specificity of each of the two miniprobes for (a) CVI988 (vaccine strain) and (b) RB1B (representative virulent strain), respectively, by plotting change in fluorescence against cycle number of the qPCR.

FIGS. 3A, 3B, 3C, and 3D show DNA standard curves of Ct value versus copy number of infected Chick Embryo Fibroblast (CEF) cells produced for the following qPCR reactions: (a) CVI988 (vaccine strain) probe with nucleic acid from CVI988 (vaccine strain) infected CEF (FIG. 3A); (b) RB1B (representative virulent strain) probe with nucleic acid from RB1B (representative virulent strain) infected CEF (FIG. 3B); (c) dual-specificity probe with nucleic acid from CVI988 (vaccine strain) infected CEF (FIG. 3C); and (d) dual-specificity probe with nucleic acid from RB1B (representative virulent strain) infected CEF (FIG. 3D). Copy number values were produced by calibrating the fluorescence results produced with those produced from plasmid DNA of known copy number.

FIG. 4 shows the specificity of the nucleic acid probes for MDV-serotype-3 vaccine HVT, MDV-serotype-2 vaccine SB-1, 3 different sources of MDV-1 vaccine CVI988 and for MDV-1 virulent strains of varying virulence across a range of 12 different virulent stains of MDV-1. Serotypes (1,2 or 3) and pathotypes (v, vv or vv+) are shown for each of the MDV-1 strains. (v=virulent, vv=very virulent, vv+=very virulent plus).

Figure 7A:
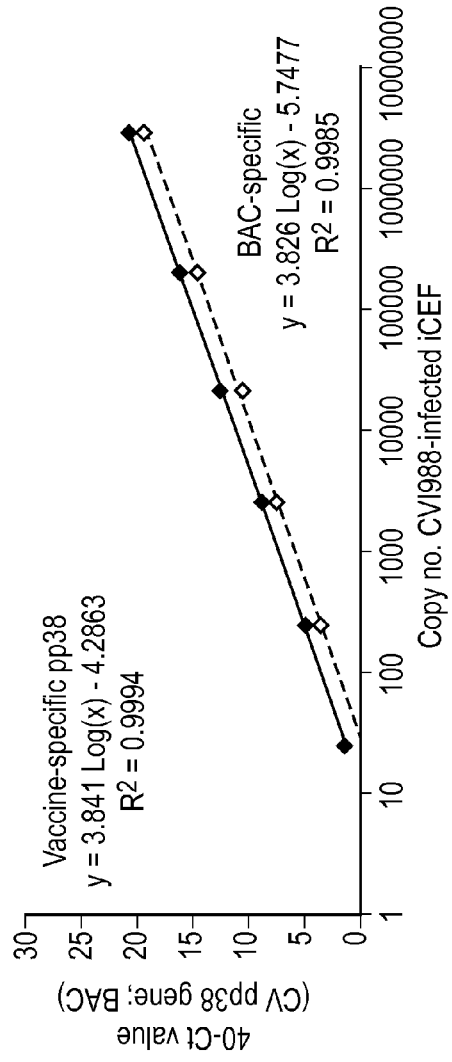
Figure 7B:
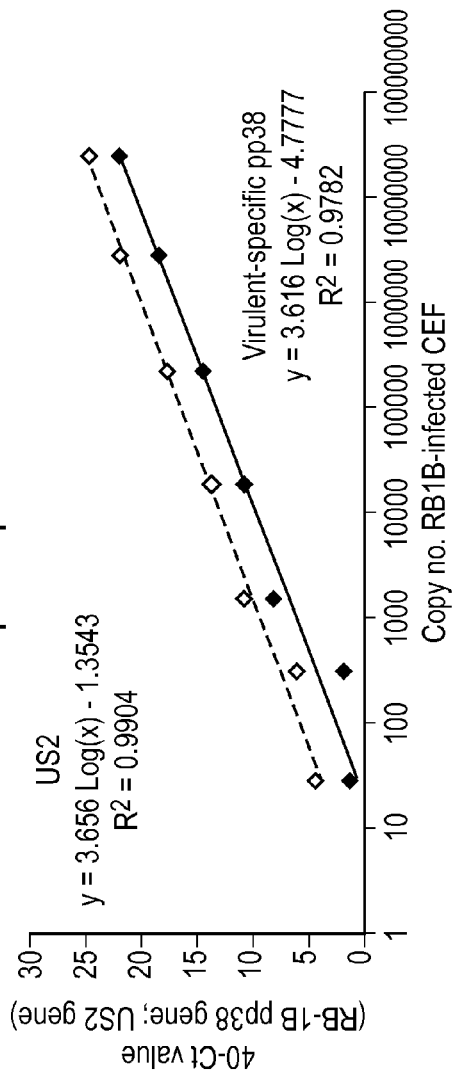

FIGS. 7A and 7B show the comparison of standard curves of Ct-values versus copy number of infected cells produced in the following qPCR reactions: (a) CVI988 (vaccine strain) probe with nucleic acid from CVI988 (vaccine strain) infected CEF (FIG. 7A); and (b) RB1B (representative virulent strain) probe with nucleic acid from RB1B (representative virulent strain) infected CEF (FIG. 7B) compared to those produced from the equivalent reactions in the BAC/US2 qPCR method.

FIGS. 8A and 8B show the copy number produced for 40 birds using qPCR systems specific for BAC cloned vaccine virus (column 1), virulent/challenge virus (column 2) and total virus (column 3) and comparing the present qPCR invention versus BAC/US2 based qPCR for each. Birds are indicated as to whether they fall into the following four groups: 1) non-vaccinated, non-challenged; 2) vaccinated, non-challenged; 3) vaccinated, challenged; and 4) non-vaccinated, challenged.

Figure 9A:
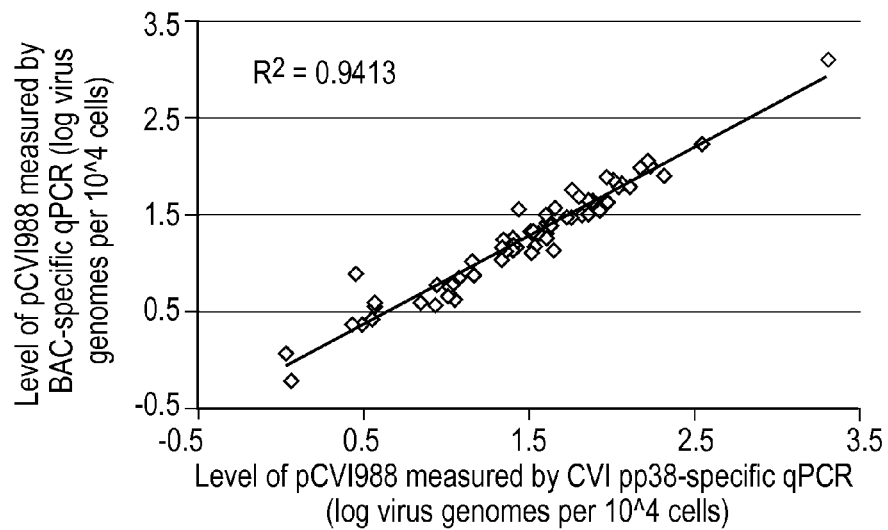
Figure 9B:
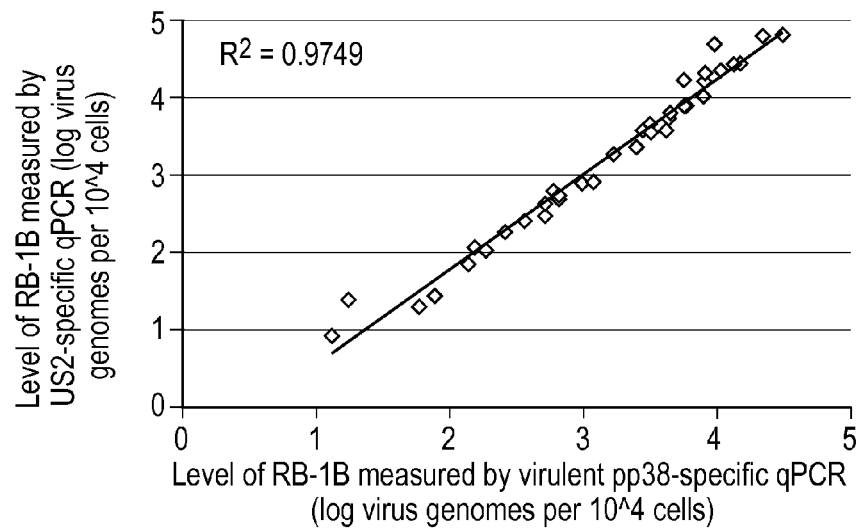

FIGS. 9A and 9B show correlation of levels of virus measured between the qPCR of the present invention and the BAC/US2 qPCR system for (a) vaccine virus and (b) virulent virus, respectively.

Figure 10A:
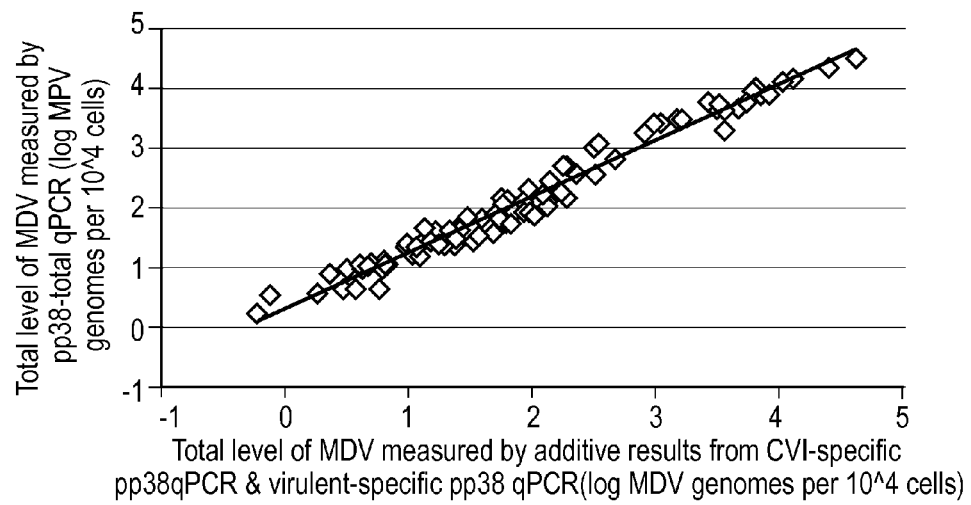
Figure 10B:
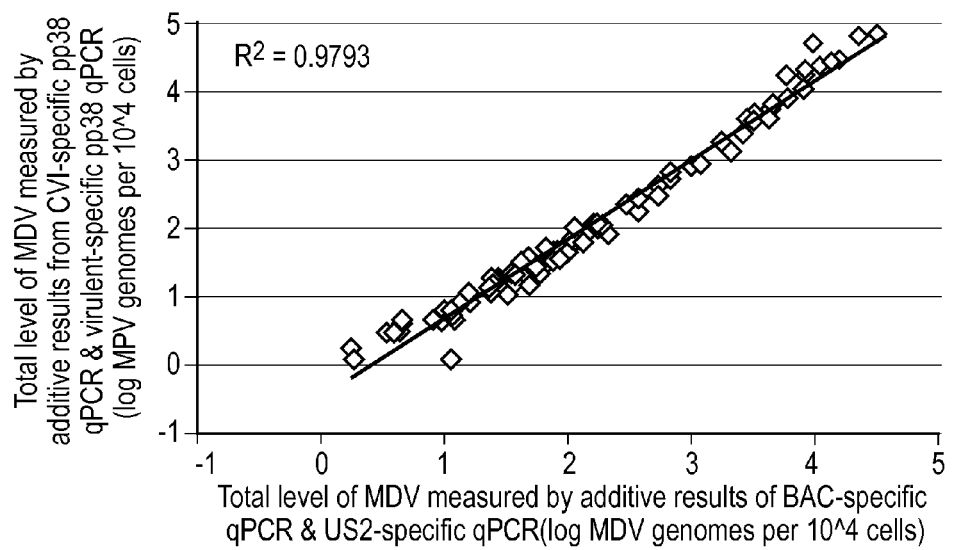
Figure 10C:
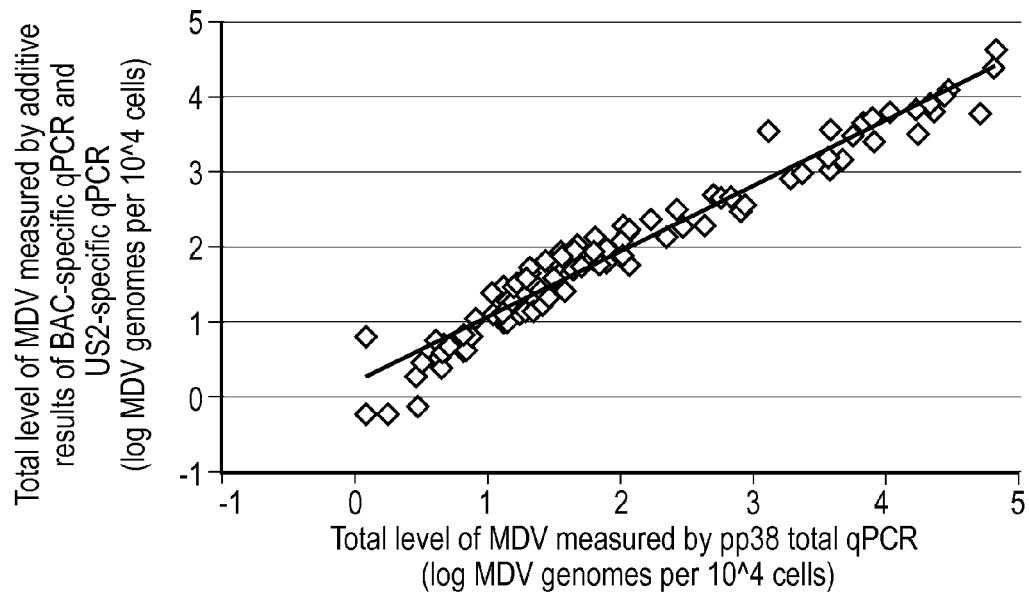

FIGS. 10A, 10B, and 10C show (a) correlation of levels of virus measured between total (dual-specific) qPCR and the additive result of vaccine-specific and virulent-specific for the qPCR of the present invention (FIG. 10A); (b) correlation of levels of virus measured between the additive result of vaccine-specific and virulent-specific for the qPCR of the present invention and the additive result of the BAC/US2 qPCR system (FIG. 10B); and (c) correlation between levels of virus measured between total (dual-specific) qPCR of the present invention and the additive result of the BAC/US2 qPCR system (FIG. 10O).

EXAMPLE 1

Design of qPCR Primers and Probes

The MDV pp38 gene sequence shows two single nucleotide differences between the attenuated vaccine CVI988 and Md5 (a virulent strain) (FIGS. 1A and 1B). The polymorphism highlighted in large bold underline (G/A) represents a consistent difference between the MDV-1 vaccine virus and the MDV-1 virulent viruses for all which we have sequence (RB1B MDV, 584A MDV, 595 MDV, 684A MDV, Md5 MDV, HPRS-B14 MDV, JM102 MDV, 660A MDV, 675A MDV, 549 MDV, 571 MDV, C12-130 MDV) and this was the polymorphism which was incorporated into the specific probes. The polymorphism highlighted in *bold underline italics (G/A)* is not consistently present in all strains of virulent virus. Table 1 lists the primer sequences together with the two probes (pp38Vacc_G_JUP specific for the attenuated vaccine CVI988; and pp38Vir_A_JUP(1) specific for virulent viruses) that were designed to cover the polymorphic region. A third probe pp38-total_JUP targeting a region common to pp38 of all MDV-1 strains was also designed. All three probes can be used in combination with the same primer pair (see Table 1).

Table 1 also shows a second probe (pp38Vir_A_JUP(3)) targeting specifically virulent viruses was designed so that the vaccine-specific, virulent-specific and total pp38 probes all have a similar melting temperature. The performance of pp38Vir_A_JUP(3) is very similar to that of pp38Vir_A_JUP (1) (the other virulent strain-specific probe); however, because it covers the second 'non-consistent' polymorphic site, it is possible that affinity for some field strains may be reduced (see FIG. 1B and Table 1). The probes are labelled with the dye JUP (AlleLogic Biosciences), which is detected in the VIC detection channel of the real-time PCR instrument.

TABLE 1

|  | CVI988 MDV1-specific pp38 PCR | Virulent MDV1-specific pp38 q-PCR | Total pp38 q-PCR |
|---|---|---|---|
| F. Primer | GAGCTAACCGGAGAGGGAGA (SEQ ID NO: 5) | GAGCTAACCGGAGAGGGAGA (SEQ ID NO: 5) | GAGCTAACCGGAGAGGGAGA (SEQ ID NO: 5) |
| R. Primer | CGCATACCGACTTTCGTCAA (SEQ ID NO: 6) | CGCATACCGACTTTCGTCAA (SEQ ID NO: 6) | CGCATACCGACTTTCGTCAA (SEQ ID NO: 6) |

TABLE 1-continued

| | CVI988 MDV1-specific pp38 PCR | Virulent MDV1-specific pp38 q-PCR | Total pp38 q-PCR |
|---|---|---|---|
| Probes available | CCCACCGTGACAGCC (SEQ ID NO: 1) pp38Vacc_G_JUP Tm = 57.7 | CCCACTGTGACAGCC (SEQ ID NO: 2) pp38Vir_A_JUP(1) Tm = 54.1 | GCTACCGCCTGAGCC (SEQ ID NO: 4) pp38-total_JUP Tm = 57.4 |
| | | CTCCCACTGTGACAGCC (SEQ ID NO: 3) pp38Vir_A_JUP(3) (*) Tm = 57.1 | |
| Probe strand | – | – | + |
| Amp. size | 99 bp | 99 bp | 99 bp |

Primers and probes were designed and manufactured by AlleLogic Biosciences, Hayward, Calif., USA.

EXAMPLE 2

Infection of Chick Embryo Fibroblast (CEF) Cells

Chick Embryo Fibroblast (CEF) cells were infected with either CVI988 vaccine strain or RB1B virulent strain of MDV-1. Five days post infection, serial dilutions were prepared from these cells for use in singleplex qPCRs.

CEF (chick embryo fibroblast) cell monolayers were established in culture 75 cm$^2$ flasks and infected with approximately 1000 plaque forming units (pfu) of cell-associated virus. After 5 days in culture at 38° C., cells were harvested and DNA was prepared using phenol-chloroform extraction method. Reactions are 25 ul volume and contain: Absolute Blue qPCR mastermix (ABgene), 400 nM of each primer (i.e. Ovo primers+virus specific primers), 200 nM of each probe (i.e. Ovo probe+virus-specific probe), approximately 100 ng DNA sample. Reactions are performed on an ABI7500 real-time PCR machine using the cycling parameters: 50° C. for 2 min, 95° C. for 15 min, followed by 40 cycles of 95° C. (15 sec) and 60° C. (1 min).

EXAMPLE 3

Specificity of the qPCRs: Singleplex Reactions

Reactions were set up essentially as previously described (Baigent et al., 2005a), each containing 'ABsolute q-PCR master mix' (ABgene, Epsom, UK), forward and reverse primer, and one of the probes. An ABI 7500FAST® q-PCR system (Applied Biosystems, Foster City, Calif., USA) was used to amplify and detect the reaction products, under the following conditions: 50° C. for 2 min, 95° C. for 15 min, followed by 40 cycles of 95° C. (15 sec) and 60° C. (1 min). Primer and probe combinations for each singleplex qPCR are shown in Table 2.

TABLE 2

| | CVI988 MDV1-specific pp38 PCR | Virulent MDV1-specific pp38 q-PCR |
|---|---|---|
| F. Primer | GAGCTAACCGGAGAGGGAGA (SEQ ID NO: 5) | GAGCTAACCGGAGAGGGAGA (SEQ ID NO: 5) |

TABLE 2-continued

| | CVI988 MDV1-specific pp38 PCR | Virulent MDV1-specific pp38 q-PCR |
|---|---|---|
| R. Primer | CGCATACCGACTTTCGTCAA (SEQ ID NO: 6) | CGCATACCGACTTTCGTCAA (SEQ ID NO: 6) |
| Probe | CCCACCGTGACAGCC (SEQ ID NO: 1) pp38Vacc_G_JUP Tm = 57.7 | CCCACTGTGACAGCC (SEQ ID NO: 2) pp38Vir_A_JUP(1) Tm = 54.1 |

Specificity of the probes was initially assessed by using serial 10-fold dilutions of DNA prepared from chick embryo fibroblast (CEF) cells, five days post infection with either CVI988 or RB1B (a virulent strain of MDV-1).

Figure 2A:
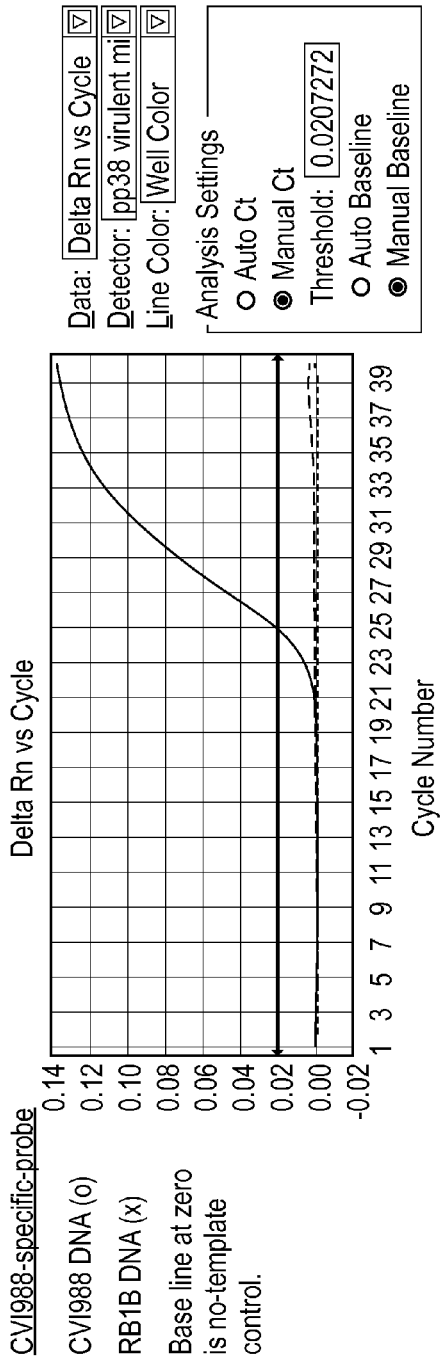
Figure 2B:
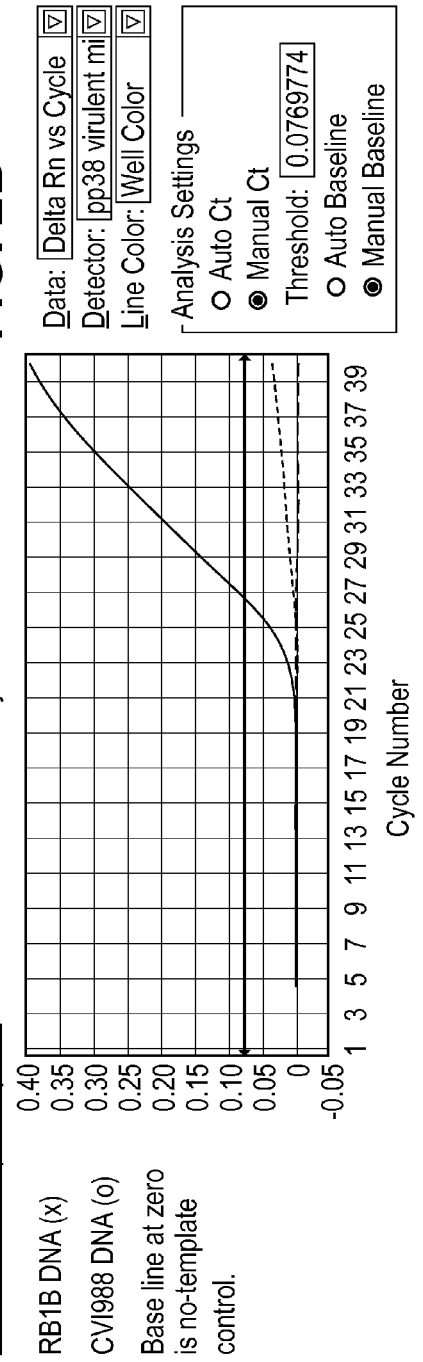

FIGS. 2A and 2B demonstrates the change in fluorescence produced by (a) CVI988-specific probe and (b) virulent-specific probe using nucleic acid template from either CVI988 or RBIB (a virulent strain) or no template control. The data clearly shows the signal to only be produced at significant levels when the probe specific for the nucleic acid is used in the qPCR and as such specificity of the probes is clearly demonstrated.

EXAMPLE 4

Standard Curves for qPCR

Figure 3A:
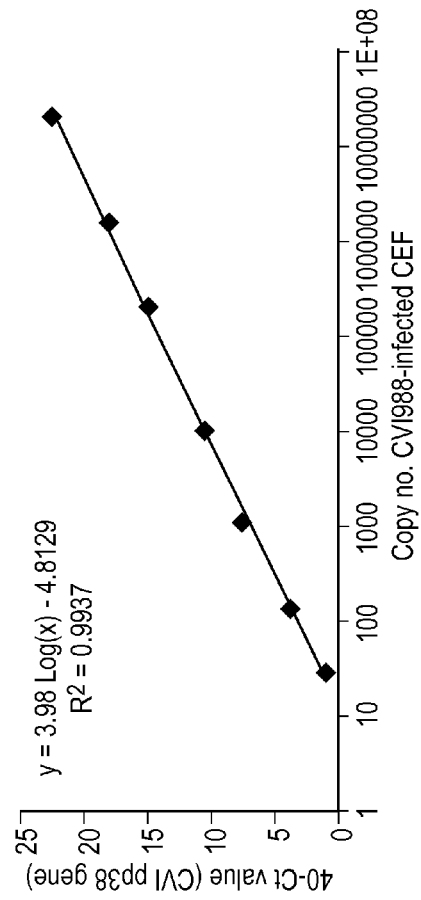
Figure 3B:
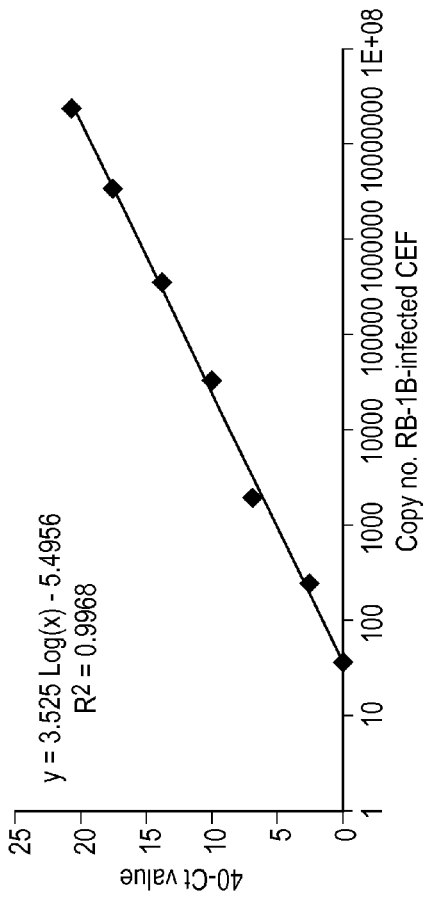
Figure 3C:
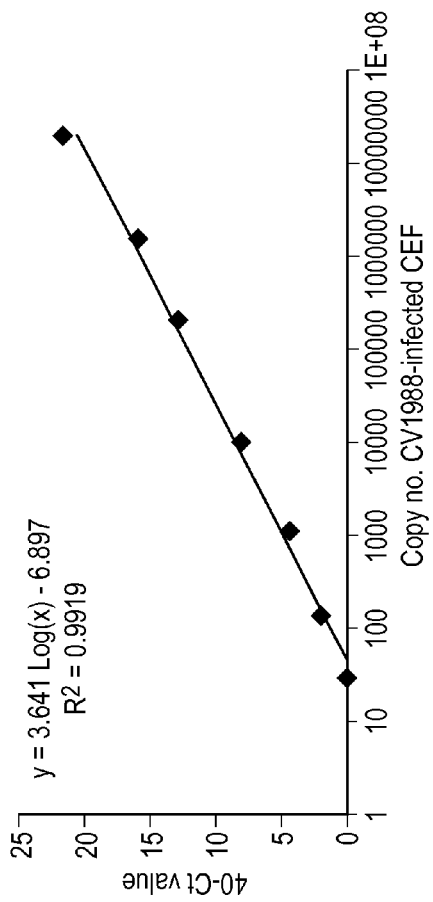
Figure 3D:
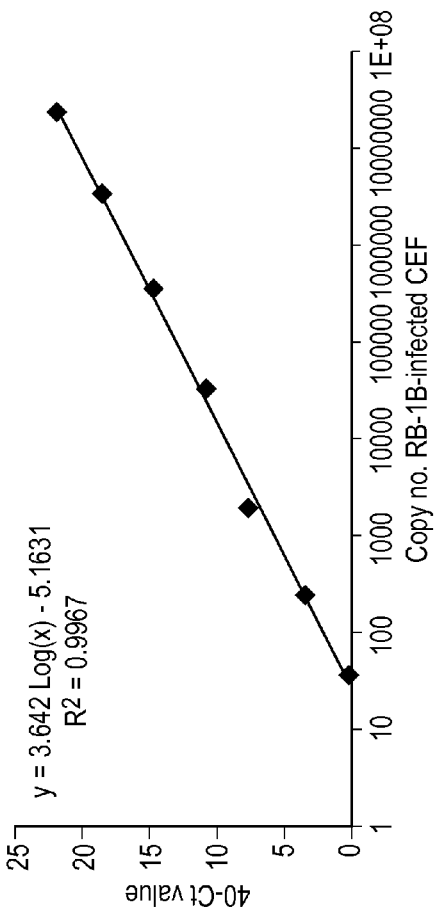

DNA standards were prepared from CVI988-infected CEF cells and from RB-1B-infected CEF cells and accurately quantified by calibration against plasmid DNA of known copy number. Ten-fold serial dilutions were prepared. FIG. 3A shows the standard curve produced using CVI988-specific qPCR on CVI988 DNA. FIG. 3B shows the standard curve produced using virulent-specific qPCR on RB-1B DNA. FIG. 3C shows the standard curve produced using total pp38 qPCR on CVI988 DNA. FIG. 3D shows the standard curve produced using total pp38 qPCR on RB-1B DNA.

Each reaction was of good efficiency, and produced a good standard curve. The pp38 total probe detected CVI988 (vaccine) DNA and RB-1B (virulent) DNA and with similar efficiency as predicted. No-template-control wells were negative for all probes.

EXAMPLE 5

Specificity of the pp38 Nucleic Acid Probes for a Range of MDV-1 Strains

The specificity of pp38Vir_A_JUP (virulent-specific) probe and pp38Vacc_G_JUP (CVI988 vaccine-specific) probes was tested on a range of 12 MDV-1 strains of varying virulence, a range of 3 different sources of MDV-1 vaccine strain CVI988 and 2 non-serotype-1 vaccine strains (FIG. 4). Thresholds (delta Rn) were set at: Ovo reaction (0.2), virulent-specific pp38 reaction (0.6), CVI988-specific pp38 reaction (0.35), total pp38 reaction (0.1). The virulent-specific probe detected all virulent strains of MDV1 (but did not detect CVI988), and the vaccine-specific probe detected only CVI988, but from all 3 sources. Neither probe detected the MDV-2 and MDV-3 vaccine strains SB-1 and HVT. The data confirm the consistent specificity of pp38Vacc_G_JUP for the MDV-1 vaccine CVI988 strain of varying sources and the specificity of pp38Vir_A_JUP for virulent MDV-1 strains of varying virulence. The data also shows specificity of both probes for MDV-1 strains over MDV-2 or MDV-3 strains.

EXAMPLE 6

Adaptation of the Assays for Absolute Quantification

In order to use the MiniProbe q-PCR reactions for absolute quantification of vaccine and challenge virus in tissue samples (expressed as virus genomes per $10^4$ cells), it was necessary to optimise duplexing of the pp38 reactions with Ovo reaction. The Ovo probe was labelled with FAM-BHQ1 so as to be detected in a different channel to the pp38 probe fluorescence. The target amplicon of the Ovo qPCR is 71 base pairs and primers and probe sequences used are shown in table 3 below. Primers and probes were produced by Sigma Aldrich and Eurogentec.

TABLE 3

| Chicken ovotransferrin gene (Jeltsch et al., 1987) | Ovo forward primer | CACTGCCACTGGGCTCTGT (SEQ ID NO: 7) | 71 bp |
|---|---|---|---|
| | Ovo reverse primer | GCAATGGCAATAAACCTCCAA (SEQ ID NO: 8) | |
| | Ovo probe | AGTCTGGAGAAGTCTGTGCAGCC TCCA (SEQ ID NO: 9) (5' FAM label, 3' BHQ label) | |

Two copies of Ovo gene is equivalent to one cell, so the Ovo standard curve can be used to calculate the Ovo Ct value which is equivalent to 10000 cells. CVI988 DNA and the CVI988-specific reaction is used to calculate the copy no. (from CVI988-specific Ct value) of CVI988 in the sample, while a standard curve produced using RB-1B DNA and the virulent-specific reaction is used to calculate the copy no. (from virulent-specific Ct value) of virulent MDV in the sample. The Ovo standard curve is used to work out Ovo copy no. (from Ovo Ct value) in the sample. Ovo copy number (i.e. cell number) will be different in different samples so, in order to be able to accurately compare sample A with sample B it is calculated how many MDV copies would be in each sample if those samples had 10000 cells.

Figure 5:
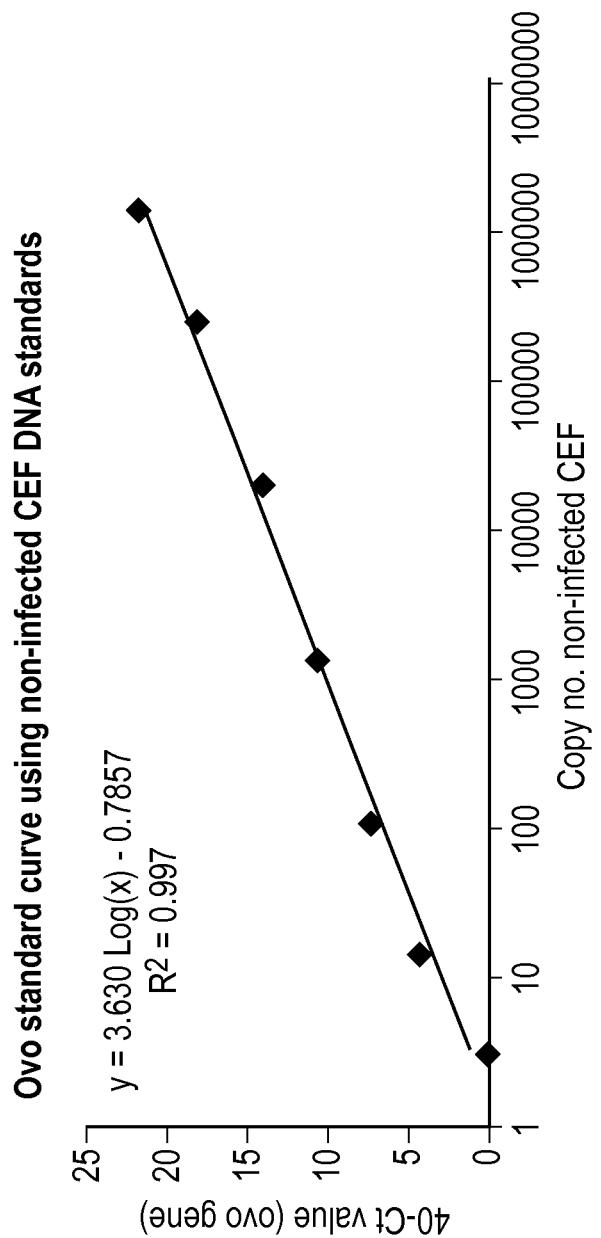
FIG. 5 shows the standard curve produced for the Ovo qPCR reaction using an Ovo probe labelled with FAM-BHQ1 and calibrated serial dilutions of non-infected Chick Embryo Fibroblast (CEF) DNA.

The standard curve for the Ovo reaction was prepared using calibrated serial dilutions of non-infected CEF DNA and is shown in FIG. 5.

EXAMPLE 7

Testing and Validation of Duplex qPCR on Chicken DNA Samples

Since the primer pair will amplify both CVI988 and virulent MDV-1 DNA, these two target sequences will compete for the same primers when both target sequences are present. Samples from laboratory experiments, and from the field, will contain CVI988 and virulent MDV-1 in various ratios. To confirm that competition for primers does not prevent the amplification (and thus detection) of the less abundant virus where one virus is present at high levels, and the other at only low levels, the ability of the reactions to accurately quantify both CVI988 and virulent MDV-1 in mixed samples was examined.

Figure 6A:
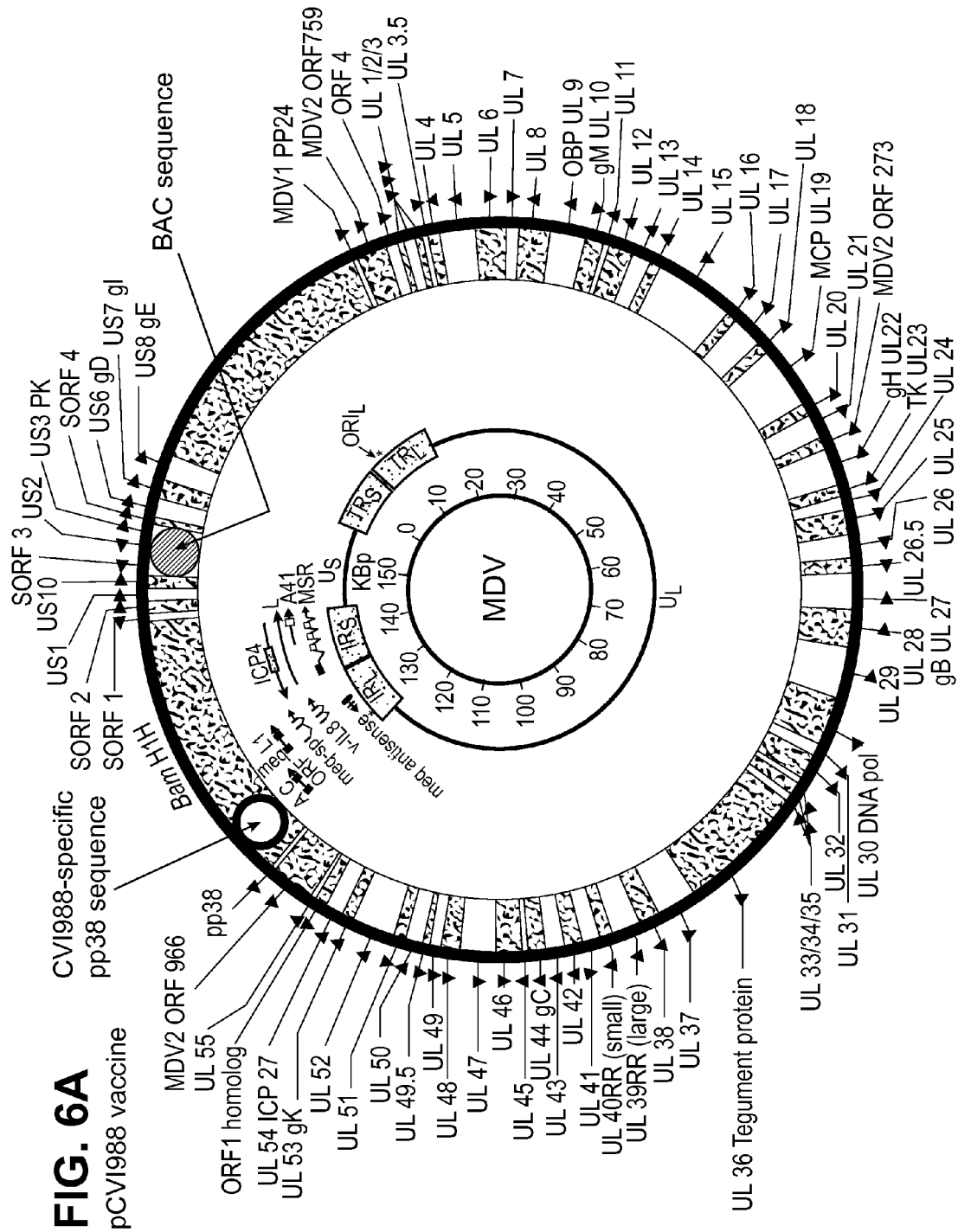
FIGS. 6A and 6B show the gene map for MDV-1 and the location of the key pp38 and US2 genes within the CVI988 vaccine and RB1B challenge virus, respectively.
Figure 6B:
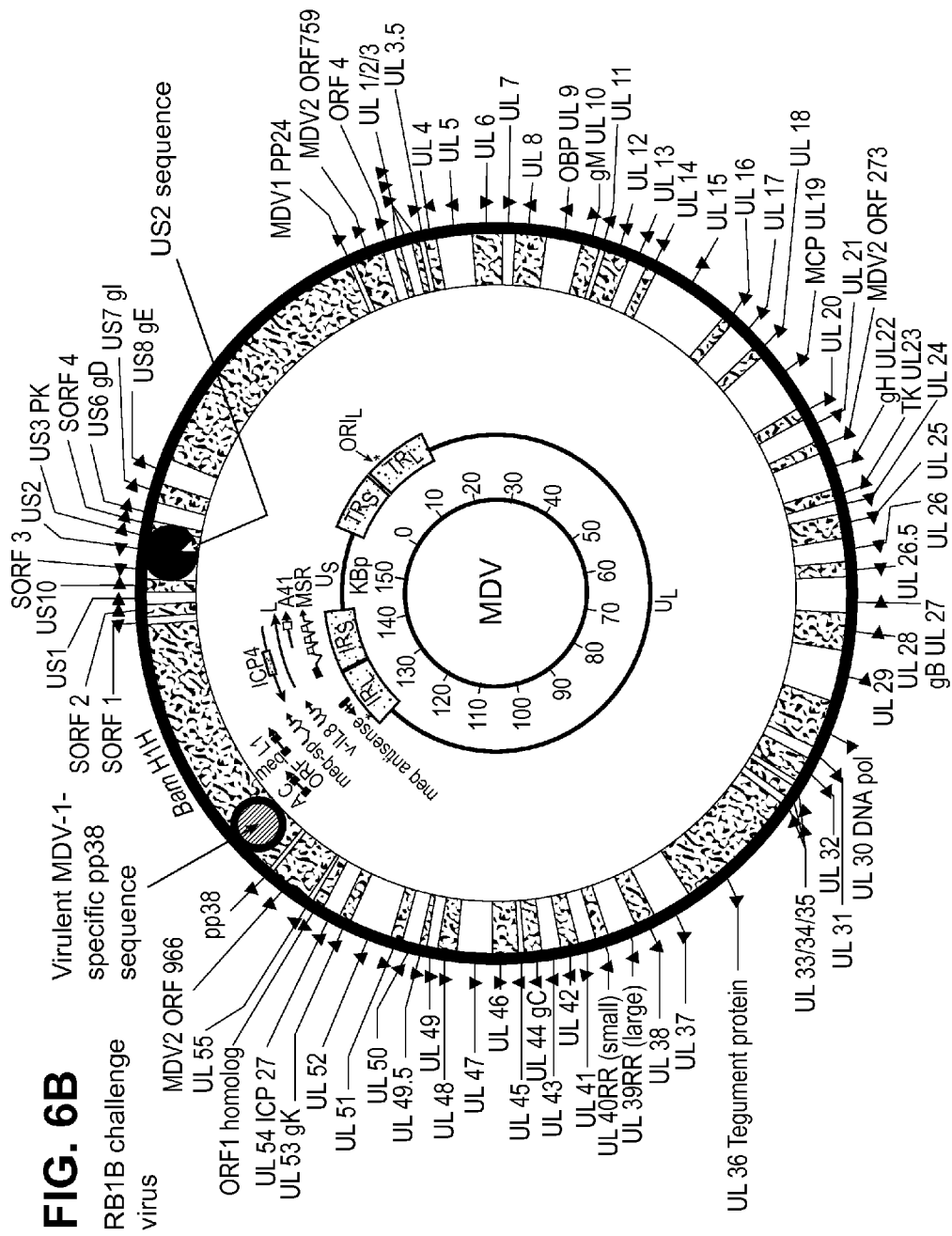

Chicken tissue DNA samples were taken from an experiment in which chickens had been vaccinated with a BAC-cloned CVI988 virus (pCVI988) and challenged with RB-1B. Four groups of chicks were (1) non-vaccinated, non-challenged; (2) vaccinated, non-challenged; (3) vaccinated and challenged; (4) non-vaccinated, challenged. Spleen samples were collected at various time points post vaccination and challenge. The vaccine virus was pCVI988 and the challenge (virulent) virus WT RB-1B which should allow distinction between the two viruses by both the CVI988 pp38/virulent pp38 system and by a second qPCR system which we have developed to distinguish between BAC cloned MDV (using a BAC-specific sequence) and wild-type MDV (by targeting the US2 gene). This latter qPCR system could thus be used to validate the CVI988 pp38/virulent pp38 qPCR system). Total virus was also measured using the pp38-total reaction. A plan for the validation of the qPCR system is shown in Table 4 and indicated on the viral gene maps of FIGS. 6A and 6B.

TABLE 4

| | Miniprobe pp38 qPCR system target | Standard qPCR system target |
|---|---|---|
| Vaccine MDV 1000 pfu, 1 d, i.m. pCVI988 | CVI988-specific pp38 sequence | BAC sequence |
| Challenge MDV 1000 pfu, 15 d, i.p. RB-1B (vvMDV-1) | Virulent 'MDV1-specific' pp38 | US2 sequence |
| Total MDV | Total pp38 | — |

Each of the five virus-specific qPCR reactions shown in Table 4 was performed in duplex with the Ovo qPCR to allow absolute quantification of virus per 10000 cells. FIGS. 7A and 7B show the standard curves used for quantifying vaccine and virulent virus using both qPCR systems.

FIGS. 8A and 8B shows level of vaccine, challenge and total MDV measured in 40 birds, from four groups, 1) non-vaccinated, non-challenged; 2) vaccinated, non-challenged; 3) vaccinated, challenged; and 4) non-vaccinated, challenged. Samples having a baseline value (0.6) are negative.

The first two columns show measurement of vaccine virus by CVI-specific pp38 qPCR (col 1) and BAC-specific qPCR (col 2). In both systems, vaccine virus was detected only in the two vaccinated groups. Agreement between the copy number values obtained with the two systems was good (see also FIG. 9A)

Columns 3 and 4 show measurement of challenge virus by virulent-specific pp38 qPCR (col 3) and US2-specific qPCR (col 4). In both systems, challenge virus was detected only in the two challenged groups. Agreement between the copy number values obtained with the two systems was good (see also FIG. 9B).

Columns 5, 6, and 7 show measurement of total MDV by pp38 qPCR to measure both viruses (col 5), additive results from CVI-specific pp38 qPCR and virulent-specific pp38 qPCR (col 6), and additive results from BAC-specific qPCR and US2-specific qPCR (col 7). Agreement between the copy number values obtained with these three systems was very good (FIGS. 10A, 10B, and 10C).

These data confirm that the CVI-pp38 qPCR and the virulent MDV1-pp38 qPCR show excellent specificity, and can be used to accurately quantify CVI988 vaccine and virulent MDV-1 strains in tissue samples including those containing both viruses in biologically relevant amounts.

REFERENCES

1. Baigent, S. J., Petherbridge, L. J., Howes, K., Smith, L. P., Currie, R. J., Nair, V. K., 2005a. Absolute quantitation of Marek's disease virus genome copy number in chicken feather and lymphocyte samples using real-time PCR. J. Virol. Methods 23, 53-64.
2. Baigent, S. J., Smith, L. P., Currie, R. J., Nair, V. K., 2005b. Replication kinetics of Marek's disease vaccine virus in feathers and lymphoid tissues using PCR and virus isolation. J Gen Virol. 86, 2989-2998.
3. Baigent, S. J., Smith, L. P., Nair, V. K., Currie, R. J., 2006. Vaccinal Control of Marek's Disease: Current challenges, and future strategies to maximize protection. Vet. Immunol. Immunopathol. 112, 78-86.
4. Becker Y, Asher Y, Tabor E, Davidson I, Malkinson M, Weisman Y: Polymerase chain reaction for differentiation between pathogenic and non-pathogenic serotype 1 Marek's disease viruses (MDV) and vaccine viruses of MDV-serotypes 2 and 3. J Virol Methods 1992; 40:307-322.
5. de Boer, G. F., Groenendal, J. E., Boerrigter, H. M., Kok, G. L., Pot, J. M., 1986. Protective efficacy of Marek's disease virus (MDV) CVI-988 CEF65 clone C against challenge infection with three very virulent MDV strains. Avian Dis. 30, 276-283.
6. Islam, A., Cheetham, B. F., Mahony, T. J., Young, P. L., Walkden-Brown, S. W., 2006a. Absolute quantitation of Marek's disease virus and Herpesvirus of turkeys in chicken lymphocyte, feather tip and dust samples using real-time PCR. J. Virol. Methods 132, 127-134.
7. Gimeno I M, Witter R L, Hunt H D, Reddy S M, Lee L F, Silva R F. The pp38 gene of Marek's disease virus (MDV) is necessary for cytolytic infection of B cells and maintenance of the transformed state but not for cytolytic infection of the feather follicle epithelium and horizontal spread of MDV. J Virol. 2005 April; 79(7):4545-9
8. Islam, A. F., Walkden-Brown, S. W., Islam, A., Underwood, G. J., Groves, P. J., 2006b. Relationship between Marek's disease virus load in peripheral blood lymphocytes at various stages of infection and clinical Marek's disease in broiler chickens. Avian Pathol. 35, 42-48.
9. King, D., Page, D., Schat, K. A., Calnek, B. W., 1981. Difference between influences of homologous and heterologous maternal antibodies on response to serotype-2 and serotype-3 Marek's disease vaccines. Avian Dis. 25, 74-81.
10. Landman, W. J., Verschuren, S. B., 2003. Titration of Marek's disease cell-associated vaccine virus (CVI988) of reconstituted vaccine and vaccine ampoules from Dutch hatcheries. Avian Dis. 47, 1458-1465.
11. Renz, K. G., Islam, A., Cheetham, B. F., Walkden-Brown, S. W., 2006. Absolute quantification using real-time polymerase chain reaction of Marek's disease virus serotype 2 in field dust samples, feather tips and spleens. J. Virol. Methods. 135, 186-191.
12. Rispens, B. H., Van Vloten, J., Mastenbroek, N., Maas, H. J. L., Schat, K. A., 1972. Control of Marek's disease in the Netherlands. I. Isolation of an avirulent Marek's disease virus (strain CVI 988) and its use in laboratory vaccination trials. Avian Dis. 16, 108-125.
13. Silva R F: Differentiation of pathogenic and non-pathogenic serotype 1 Marek's disease viruses (MDVs) by the polymerase chain reaction amplification of the tandem direct repeats within the MDV genome. Avian Dis 1992; 36:521-528.
14. Sambrook and Russell: Molecular Cloning: A Laboratory Manual. Volume 1-3 (2001 $3^{rd}$ Ed)

The invention claimed is:

1. A kit of parts for the discrimination between and quantification of a vaccine strain and a virulent strain of Marek's Disease Virus Serotype-1 (MDV-1) in a sample from a bird, the kit comprising:
   (i) primers that will amplify a region of the pp38 gene incorporating a consistent single nucleotide polymorphism (SNP) difference between vaccine and virulent strains of MDV-1 said SNP being a G/A polymorphism located at position 320 of the sequences of FIG. 1 ((a) and (b));
   (ii) a detectable nucleic acid probe specific for the SNP of the vaccine strain of MDV-1; and
   (iii) at least one detectable nucleic acid probe specific for the SNP of the virulent strain of MDV-1, wherein the specific nucleic acid probes of (ii) and (iii) are each labelled with at least one signal-generating dye and wherein the probes compromise the following sequences:
   vaccine strain specific probe sequence: 5' CCCACCGTGACAGCC 3' (SEQ ID NO: 1); and at least one of the following virulent strain-specific probe sequences: 5' CCCACTGTGACAGCC 3' (SEQ ID NO: 2) and 5' CTCCCACTGTGACAGCC 3' (SEQ ID NO: 3).

2. The kit of claim 1 wherein the kit further comprises standard qPCR reagents.

3. The kit of claim 1 further comprising reagents required for a known standard qPCR utilizing a probe labelled with a different signal-generating dye than that of each of the specific nucleic acid probes of (ii) and (iii) to allow absolute quantification of the vaccine and virulent strains.

4. The kit of claim 1 wherein the vaccine strain is the CVI1988 vaccine.

5. The kit of claim 1 wherein the kit further comprises a total probe that binds both the vaccine strain and the virulent strain.

6. The kit of claim 5 wherein the total probe comprises the following sequence:

```
                                           (SEQ ID NO: 4)
        5' GCTACCGCCTGAGCC 3'.
```

7. The kit of claim 1 wherein the primers are:

```
Forward primer:
                                           (SEQ ID NO: 5)
5' GAGCTAACCGGAGAGGGAGA 3';
and Reverse primer:
                                           (SEQ ID NO: 6)
5' CGCATACCGACTTTCGTCAA 3'.
```

8. The kit of claim 1 wherein the virulent MDV strain is selected from RB1B MDV, 584A MDV, 595 MDV, 684A MDV, Md5 MDV, HPRS-B14 MDV, JM102 MDV, 660A MDV, 675A MDV, 549 MDV, 571 MDV, or C12-130 MDV.

* * * * *

SEQUENCE LISTING

```
<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: Vaccine strain-specific probe pp38Vacc_G_JUP

<400> SEQUENCE: 1
cccaccgtga cagcc                                                    15

<210> SEQ ID NO 2
<211> LENGTH: 15
```

<212> TYPE: DNA
<213> ORGANISM: Artificial Sequence
<220> FEATURE:
<223> OTHER INFORMATION: Virulent strain-specific probe pp38Vir_A_JUP(1)

<400> SEQUENCE: 2
cccactgtga cagcc                                                    15

<210> SEQ ID NO 3
<211> LENGTH: 17
<212> TYPE: DNA
<213> ORGANISM: Artificial Sequence
<220> FEATURE:
<223> OTHER INFORMATION: Virulent strain-specific probe pp38Vir_A_JUP(3)

<400> SEQUENCE: 3
ctcccactgt gacagcc                                                  17

<210> SEQ ID NO 4
<211> LENGTH: 15
<212> TYPE: DNA
<213> ORGANISM: Artificial Sequence
<220> FEATURE:
<223> OTHER INFORMATION: Total probe pp38-total_JUP

<400> SEQUENCE: 4
gctaccgcct gagcc                                                    15

<210> SEQ ID NO 5
<211> LENGTH: 20
<212> TYPE: DNA
<213> ORGANISM: Artificial Sequence
<220> FEATURE:
<223> OTHER INFORMATION: pp38 forward primer

<400> SEQUENCE: 5
gagctaaccg gagagggaga                                               20

<210> SEQ ID NO 6
<211> LENGTH: 20
<212> TYPE: DNA
<213> ORGANISM: Artificial Sequence
<220> FEATURE:
<223> OTHER INFORMATION: pp38 reverse primer

<400> SEQUENCE: 6
cgcataccga ctttcgtcaa                                               20

<210> SEQ ID NO 7
<211> LENGTH: 19
<212> TYPE: DNA
<213> ORGANISM: Artificial Sequence
<220> FEATURE:
<223> OTHER INFORMATION: Ovo forward primer

<400> SEQUENCE: 7
cactgccact gggctctgt                                                19

<210> SEQ ID NO 8
<211> LENGTH: 21
<212> TYPE: DNA
<213> ORGANISM: Artificial Sequence
<220> FEATURE:
<223> OTHER INFORMATION: Ovo reverse primer

<400> SEQUENCE: 8
gcaatggcaa taaacctcca a                                            21

<210> SEQ ID NO 9
<211> LENGTH: 27
<212> TYPE: DNA
<213> ORGANISM: Artificial Sequence
<220> FEATURE:
<223> OTHER INFORMATION: Ovo probe

<400> SEQUENCE: 9
agtctggaga agtctgtgca gcctcca                                      27

<210> SEQ ID NO 10
<211> LENGTH: 873
<212> TYPE: DNA
<213> ORGANISM: Mardivirus gallid herpesvirus 2

<400> SEQUENCE: 10
atggaattcg aagcagaaca cgaagggctg acggcgtctt gggtcgcccc cgctccccag   60
ggtggaaaag gggcggaggg ccgcgcaggg gtcgccgacg aggcagggca tgggaaaaca  120
gaagcggaat gcgccgagga cggcgagaaa tgcggggacg ccgagatgag cgctttggat  180
cgggtccaga gggaccggtg gagattcagt tctccgcccc ctcactctgg agtcacgggg  240 aaggggggcta ttccaataaa gggtgatggg aaggcgatag aatgccagga gctaaccgga  300
gagggagagt ggctgtcacg gtgggggggag ctaccgcctg agccccggag gtcagggaat  360
gaacatcttg acgaaagtcg gtatgcgaaa caaaccgaaa ggggtagctc tacggggaaa  420
gaagagggag atggtatgaa gcagatgggg gagcttgccc agcagtgcga aggaggaaca  480
tatgcggact tgcttgtcga agcagagcaa gctgttgtac attccgttcg cgcattaatg  540
ctggccgaaa gacaaaaccc aaatatattg ggggagcatt tgaataaaaa acgggttctt  600
gtacaacgac cccgtactat tctatccgtg gagtcagaga atgcaacaat gcgttcttat  660
atgctggtta cattgatctg ttctgcaaaa tcattattac taggatcgtg catgtcatttt  720 ttcgctggta tgttagtcgg tagaacggca gacgtaaaaa caccattatg ggatactgta  780
tgtttgttaa tggctttctg tgcaggcatt gtcgttgggg gagtggattc tggggaggtg  840
gaatctggag aaacaaaatc tgaatcaaat taa                               873

<210> SEQ ID NO 11
<211> LENGTH: 873
<212> TYPE: DNA
<213> ORGANISM: Mardivirus gallid herpesvirus 2

<400> SEQUENCE: 11
atggaattcg aagcagaaca cgaagggctg acggcgtctt gggtcgcccc cgctccccag   60
ggtggaaaag gggcggaggg ccgcgcaggg gtcgccgacg aggcagggca tgggaaaaca  120
gaagcggaat gcgccgagga cggcgagaaa tgcggggacg ccgagatgag cgctttggat  180
cgggtccaga gggaccggtg gagattcagt tctccgcccc ctcactctgg agtcacgggg  240 aaggggggcta ttccaataaa gggtgatggg aaggcgatag aatgccagga gctaaccgga  300
gagggagagt ggctgtcaca gtgggaggag ctaccgcctg agccccggag gtcagggaat  360
gaacatcttg acgaaagtcg gtatgcgaaa caaaccgaaa ggggtagctc tacggggaaa  420
gaagagggag atggtatgaa gcagatgggg gagcttgccc agcagtgcga aggaggaaca  480
tatgcggact tgcttgtcga agcagagcaa gctgttgtac attccgttcg cgcattaatg  540
ctggccgaaa gacaaaaccc aaatatattg ggggagcatt tgaataaaaa acgggttctt  600

```
gtacaacgac cccgtactat tctatccgtg gagtcagaga atgcaacaat gcgttcttat        660
atgctggtta cattgatctg ttctgcaaaa tcattattac taggatcgtg catgtcattt        720
ttcgctggta tgttagtcgg tagaacggca gacgtaaaaa caccattatg ggatactgta        780
tgtttgttaa tggctttctg tgcaggcatt gtcgttgggg gagtggattc tggggaggtg        840
gaatctggag aaacaaaatc tgaatcaaat taa                                    873
```